(12) United States Patent
Yun et al.

(10) Patent No.: US 7,183,547 B2
(45) Date of Patent: Feb. 27, 2007

(54) ELEMENT-SPECIFIC X-RAY FLUORESCENCE MICROSCOPE AND METHOD OF OPERATION

(75) Inventors: Wenbing Yun, Walnut Creek, CA (US); Kenneth W. Nill, Lexington, MA (US)

(73) Assignee: Xradia, Inc., Concord, CA (US)

( * ) Notice: Subject to any disclaimer, the term of this patent is extended or adjusted under 35 U.S.C. 154(b) by 0 days.

(21) Appl. No.: 10/995,642

(22) Filed: Nov. 23, 2004

(65) Prior Publication Data
US 2005/0109936 A1 May 26, 2005

Related U.S. Application Data

(62) Division of application No. 10/157,089, filed on May 29, 2002.

(51) Int. Cl.
*G01N 23/00* (2006.01)
*G21K 7/00* (2006.01)

(52) U.S. Cl. ............... 250/310; 378/43; 378/73
(58) Field of Classification Search ............... 250/310, 250/306, 307
See application file for complete search history.

(56) References Cited

U.S. PATENT DOCUMENTS 4,519,092 A * 5/1985 Albert .................. 378/45

(Continued)

FOREIGN PATENT DOCUMENTS

DE 44 32 811 A1 3/1995

(Continued)

OTHER PUBLICATIONS

Kagoshima, Y., et al., "Focusing Properties of Tantalum Phase Zone Plate and its Application to Hard X-Ray Microscope," Sixth International Conference on X-Ray Microscopy, Berkeley, Ca, USA, Aug. 2-6, pp. 668-671, 1999.

(Continued)

*Primary Examiner*—Nikita Wells
*Assistant Examiner*—Johnnie L Smith, II
(74) *Attorney, Agent, or Firm*—Houston Eliseeva LLP (57) ABSTRACT

An element-specific imaging technique utilizes the element-specific fluorescence X-rays that are induced by primary ionizing radiation. The fluorescence X-rays from an element of interest are then preferentially imaged onto a detector using an optical train. The preferential imaging of the optical train is achieved using a chromatic lens in a suitably configured imaging system. A zone plate is an example of such a chromatic lens; its focal length is inversely proportional to the X-ray wavelength. Enhancement of preferential imaging of a given element in the test sample can be obtained if the zone plate lens itself is made of a compound containing substantially the same element. For example, when imaging copper using the Cu Lα spectral line, a copper zone plate lens is used. This enhances the preferential imaging of the zone plate lens because its diffraction efficiency (percent of incident energy diffracted into the focus) changes rapidly near an absorption line and can be made to peak at the X-ray fluorescence line of the element from which it is fabricated. In another embodiment, a spectral filter, such as a multilayer optic or crystal, is used in the optical train to achieve preferential imaging in a fluorescence microscope employing either a chromatic or an achromatic lens.

17 Claims, 6 Drawing Sheets

U.S. PATENT DOCUMENTS

| | | | |
|---|---|---|---|
| 4,525,853 A | 6/1985 | Keem et al. | |
| 4,870,674 A | 9/1989 | Schmahl et al. | |
| 5,192,869 A | 3/1993 | Kumakhov | |
| 5,222,113 A | 6/1993 | Thieme et al. | |
| 5,497,008 A * | 3/1996 | Kumakhov | 250/505.1 |
| 5,742,658 A | 4/1998 | Tiffin et al. | |
| 5,778,039 A * | 7/1998 | Hossain et al. | 378/45 |
| 5,864,599 A * | 1/1999 | Cowan et al. | 378/43 |
| 5,880,467 A * | 3/1999 | Martinis et al. | 250/310 |
| 6,028,911 A | 2/2000 | Kawahara | |
| 6,233,307 B1 * | 5/2001 | Golenhofen | 378/45 |
| 6,396,899 B2 | 5/2002 | Kuwabara | |
| 6,442,231 B1 * | 8/2002 | O'Hara | 378/45 |
| 6,754,304 B1 * | 6/2004 | Kumakhov | 378/45 |
| 2003/0223536 A1 * | 12/2003 | Yun et al. | 378/45 |

FOREIGN PATENT DOCUMENTS

| | | |
|---|---|---|
| DE | 195 40 195 A1 | 5/1997 |
| EP | 0 459 833 A2 | 12/1991 |
| EP | 0 423 763 B1 | 5/1994 |
| JP | 01119800 | 5/1989 |
| JP | 06003294 | 1/1994 |
| JP | 08210996 | 8/1996 |
| WO | WO 95/24638 | 9/1995 |

OTHER PUBLICATIONS

Yun, W., et al., "X-Ray Imaging and Microspectroscopy of Plants and Fungi," Journal of Synchrotron Radiation, vol. 5, Part 6 (1998).

Skala, M., "Imaging X-Ray Fluorescence using Microchannel Plate (MCP) Optics," Physics Department, Washington State University, Pullman, WA 99163 (2000), http://www.lns.cornell.edu/public/reu/2000reports/skala.pdf.

"X-Ray Fluorescence Tomography with a Woller Mirror X-Ray Microscope," Instrumentation & Techniques, pp. 70-71, Spring8, (1998-1999), http://www.spring8.or.jp/ENGLISH/publication/res_fro/RF98-99/p70-p71.pdf.

"High Resolution Scanning X-ray Fluorescence Microscopy," PSI Annual Report, (2000), http://lmn.web.psi.ch/annrep/nf0007.pdf.

* cited by examiner

ELEMENT-SPECIFIC X-RAY FLUORESCENCE MICROSCOPE AND METHOD OF OPERATION

RELATED APPLICATIONS

This application is a Divisional of U.S. application Ser. No. 10/157,089, filed May 29, 2002 which is incorporated herein by reference in its entirety.

BACKGROUND OF THE INVENTION

A number of techniques exist for the elemental analysis of objects using X-rays. Some of these techniques rely on the different X-ray attenuation characteristics of elements, whereas others rely on X-ray fluorescence.

An example of an attenuation-based analysis technique utilizes characteristic elemental resonance energies. The attenuation of an X-ray beam of a sufficiently narrow spectral bandwidth increases substantially, when the central energy increases over the resonance energy of a constituent element of a test object. X-ray microscopes taking advantage of this characteristic have been developed for element-specific imaging. The microscopes typically combine a source, such as a synchrotron, a monochromator, a lens, such as a zone plate lens, a detector array, and possibly a scintillator to generate an image of a given test object. Typically, the microscopes are used in transmission. Two images at X-ray energies below and above the resonance energy of the element of interest are often required to obtain the necessary contrast between the element of interest and other constituent elements of the test object to thereby yield an image of the element's distribution within the test object.

X-ray fluorescence analysis or spectrometry (XRF) is a nondestructive analysis technique, which uses primary radiation, such as X-rays or energetic electrons, to eject inner-shell electrons from the atoms of the test object, yielding electron vacancies in the inner shells. When outer-shell electrons in the atoms fill the vacancies, secondary radiation is emitted with energies equal to the energy difference between the inner- and outer-shell electron states. The fluorescence emissions are characteristic of different elements. Thus, measurement of the spectrum of the secondary X-rays yields a quantitative measure of the relative abundance of each element that is present in the test sample.

Element-specific imaging of a test object with a spatial resolution better than about 1 micrometer is obtained currently by analyzing the X-ray fluorescence spectrum at each point by raster scanning a small probe of ionizing radiation, such as X-rays or energetic electrons, across the test object. Element specific imaging with a spatial resolution approaching 100 nanometers (nm) has been demonstrated with high elemental sensitivity using a high brightness synchrotron radiation source, but the serial nature of the raster scanning significantly limits the throughput and the high source brightness requirement makes it unpractical for producing an element-specific imaging system using a laboratory x-ray source.

SUMMARY OF THE INVENTION

The present invention is directed to an X-ray analysis technique that relies on the generation of secondary radiation from the test object. The invention enables high resolution, high contrast imaging of structures within a test object based on their elemental composition or absorption. It also enables the elemental analysis of the test object.

In more detail, an element-specific imaging technique is disclosed that utilizes the element-specific fluorescence X-rays that are induced by primary ionizing radiation. The fluorescence X-rays from an element of interest are then preferentially imaged onto a detector using an optical train.

In one embodiment, the preferential imaging of the optical train is achieved using a chromatic lens in a suitably configured imaging system. A zone plate is an example of such a chromatic lens; its focal length is inversely proportional to the X-ray wavelength.

This embodiment of the present invention relies on both the imaging and chromatic properties of the chromatic lens to image an element of interest in a test object by appropriately configuring the imaging system to form images on the detector array of the characteristic fluorescence X-rays from the test object. A given element in the test sample can be imaged using its fluorescence X-rays. If a zone plate is used as the chromatic lens, the preferential imaging of the element can be enhanced if the plate itself is made of a compound including the same element. For example, when imaging copper using the Cu L$\alpha$ spectral line, a copper zone plate lens is used. This enhances the preferential imaging of the zone plate lens because its diffraction efficiency (percent of incident energy diffracted into the focus) changes rapidly near an absorption line and can be made to peak at the X-ray fluorescence line of the element from which it is fabricated.

In another embodiment, a spectral filter, such as a thin film filter or crystal, is used in the optical train.

Wavelength dispersive elements can be used in the optical train between the object of interest and the detector to improve preferential imaging.

According to the invention, primary ionizing radiation emitted by a radiation source impinges on a test object and excites elements within the test object to emit secondary X-ray fluorescence radiation. The secondary X-ray fluorescence radiation that is emitted by the test object from an element of interest is then preferentially imaged on a detector system, using a lens with an appropriate imaging configuration. In some examples, the distribution of the secondary radiation is of interest, whereas in other implementations, the secondary radiation is used as backlighting.

The preferential imaging is achieved, in one embodiment, by using a zone plate lens that will focus only a narrow band of energies around the fluorescence line of the element of interest onto the detector system in a suitably configured imaging system. This property results from the dependence of the focal length of a zone plate on the wavelength of radiation and thus only one wavelength satisfies the imaging condition for a given microscope configuration (object-to-lens and lens-to-detector distances).

It is recognized that element-specific imaging using a zone plate's high order diffraction, such as the $3^{rd}$ order diffraction, offers significantly better elemental specificity than using the primary $1^{st}$ order diffraction. Generally, a zone plate's focusing efficiency for higher order diffraction is smaller than the primary $1^{st}$ order diffraction.

A central stop on the zone plate may be required or desirable to obtain high signal to noise in the image formed on the detector by the fluorescence x-rays of interest by reducing or eliminating the x-rays photons that are not focused by the zone plate.

According to another embodiment, the preferential imaging is also achieved by a combination of an imaging system employing a chromatic or nonchromatic imaging optic, such as a zone plate or a suitably configured mirror (e.g., Wolter optic), and a wavelength dispersive device such as a suitably designed multilayer optic. This optic is configured to reflect efficiently the fluorescence x-rays from the element of interest while maintaining the necessary imaging properties of the imaging system. More specifically, the x-ray fluorescence microscope includes a condenser relaying the primary ionizing radiation to the test object, a mechanical stage for manipulating the test object, a zone plate, a wavelength dispersive optic such as a multilayer coating or crystal, and a detector such as detector array.

Alternatively, the x-ray fluorescence microscope includes a condenser for relaying the primary ionizing radiation to the test object, a mechanical stage for manipulating the test object, a suitably figured reflective imaging optic such as a Wolter optic, a wavelength dispersive optic such as a multilayer filter, and a detector such as detector array. It is recognized that the preferential imaging can be further improved by using a filter of high transmission of the fluorescence x-rays of interest but low transmission for some x-rays of energies substantially different from that of the fluorescence x-rays.

In one implementation of the present invention, an X-ray fluorescence microscope includes a primary ionizing radiation source, a condenser relaying the primary ionizing radiation to the test object, a mechanical stage for manipulating the test object, a zone plate lens, and a detector such as detector array.

In the preferred implementation of the X-ray fluorescence microscope, a given element is imaged by using a zone plate made of a compound comprising the same element, or a compound consisting essentially of the same element. The object-to-lens and lens-to-detector distances of the X-ray fluorescence microscope are typically configured to image a characteristic X-ray fluorescence line of an element in a test object, and the recorded image thus represents the distribution of the element. Images of other elements in the object are obtained using configurations appropriate for their respective X-ray fluorescence lines. This imaging mode is referred to as X-ray fluorescence imaging mode.

In another embodiment, the X-ray fluorescence microscope is configured for a specific characteristic fluorescence X-ray line of an element in the object with a known structure to image structures within a volume defined by the field of view and the depth of focus of the microscope using the illumination provided by the fluorescence from the element. This imaging mode is referred to as X-ray fluorescence backlighting imaging mode.

In yet another embodiment, the X-ray fluorescence microscope is configured for a specific characteristic fluorescence line of an element but all of the X-ray fluorescence signals are integrated to measure the total amount of an element within a specific volume. Amount of other elements are measured using microscope configurations appropriate for their respective X-ray fluorescence lines. This X-ray fluorescence microscope mode is referred to as fluorescence spectrometer mode.

It is recognized that the test object can be illuminated with an illumination beam with a large solid angle for increasing the rate of the secondary x-ray fluorescence generation. It is further recognized that the throughput of the x-ray fluorescence microscope can be improved by optimization of the illumination system, which typically comprises the source and the condenser, to increase the production rate of the secondary fluorescence x-rays within the volume of interest in the test object. An example of such a design includes a fine focus x-ray source specifically designed for high brightness applications and an x-ray condenser specifically designed for collecting primary ionizing x-rays from the source over a large solid angle and directing them onto the test object.

In other embodiments, multiple imaging systems are used to increase throughput and/or perform stereoscopic or tomographic imaging.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
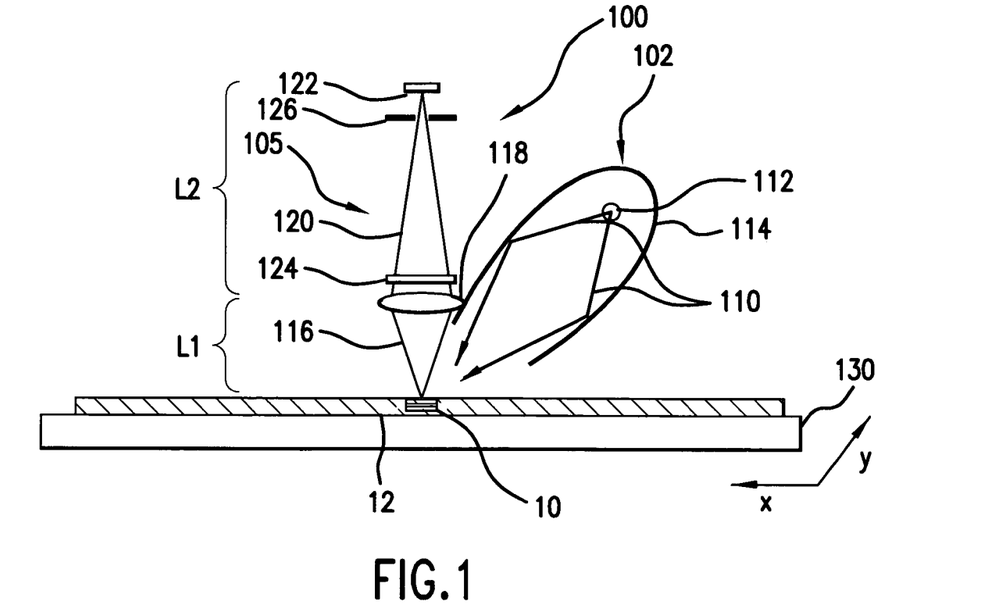
FIG. 1 is schematic diagram of an X-ray fluorescence microscope according to the present invention.

FIG. 1 shows an X-ray fluorescence microscope 100, which has been constructed according to the principles of the present invention.

Specifically, a test object, such as the integrated circuit (IC) 10 of a semiconductor wafer 12, is irradiated by primary ionizing radiation 110 such as electrons or X-rays from a radiation generator 102.

In the preferred embodiment, the wafer/test object is held on precision x-y stage 130 to position the test sample in the x-ray fluorescence microscope 100.

In one example, the primary X-ray radiation 110 is generated by source 112, by bombarding a solid target with energetic electrons, or by focusing a sufficiently intense laser beam on a solid or liquid target.

In the illustrated example, a condenser 114, such as a suitably shaped capillary tube, with or without multilayer coatings, is used to concentrate and relay the primary radiation 110 to a small area on the test object 10, which is placed correctly by control of the x-y stage 130 holding the test object 10. Other types of x-ray condensers, such as polycapillary and bent crystal, are used in alternative implementations.

The condenser 114 increases the flux density at the test object 10 and thus maximizes the induced secondary fluorescence X-rays. The test object is preferably illuminated with an illumination beam with a large solid angle. This increases the rate of the secondary x-ray fluorescence generation. This property is important for effective utilization of laboratory x-ray sources because they typically emit x-rays over a large solid angle.

In principle, the acceptable solid angle can be as high as 2 pi steradians. A lower solid angle of about 1 steradian is desirable.

The energy of the primary radiation 110 is selected in order to induce fluorescence in an element of interest. For example, with X-rays as the primary radiation, the following elements exhibit sharply increased absorption of radiation at or above the respective absorption edges: Oxygen at 543 electron-Volts (eV); silicon at 99.8 and 1839 eV; aluminum at 1560 eV; copper at 933 and 8979 eV; tantalum at 2389 eV; phosphorus at 2145 eV; and boron at 188 eV.

In some implementations when using x-rays as the primary radiation, it is recognized that selection of the x-ray energy is important to the performance of the x-ray fluorescence microscope. Sometimes, it may be beneficial to select an energy of the primary X-ray radiation to reduce or eliminate excitation of certain other elements in the test object to thereby increase the signal-to-noise ratio of the fluorescence X-rays from the element(s) of interest. Sometimes, it may be beneficial to select an energy of the primary x-ray radiation to be sufficiently higher than the absorption edge of the element of interest. This provides for a large energy separation between the secondary fluorescence x-rays and other x-rays arriving at the detector by means of elastic and Compton scattering of the primary x-rays. The energy of the primary X-ray radiation may also be selected to achieve a desired probing depth because the depth of excitation changes with the incident X-ray energy.

In some other implementations, the primary radiation is a finely focused electron beam, such as from a scanning electron microscope (SEM) or from an electron gun operating with electron energy greater than the absorption-edge energy of the element of interest. Typically, an electron energy that is three-to-four times the absorption-edge energy is selected to obtain a high ratio of the X-ray fluorescence signal to "bremstrahlung" continuum radiation background. The electron energy is also selected to obtain a desired probing depth. Sometimes, the electron energy is selected to be below absorption edges of some elements in the test object to improve signal to noise ratio in the fluorescence x-ray image.

Figure 2:
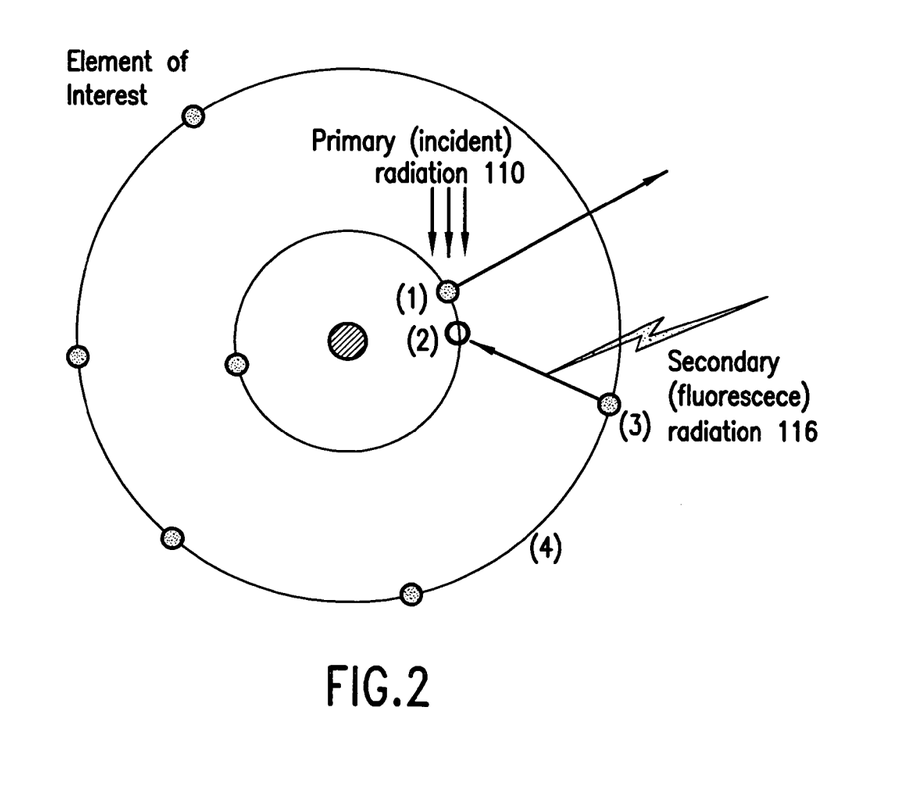
FIG. 2 is a schematic diagram illustrating radiation-induced x-ray fluorescence in an element of interest.
Figure 3:
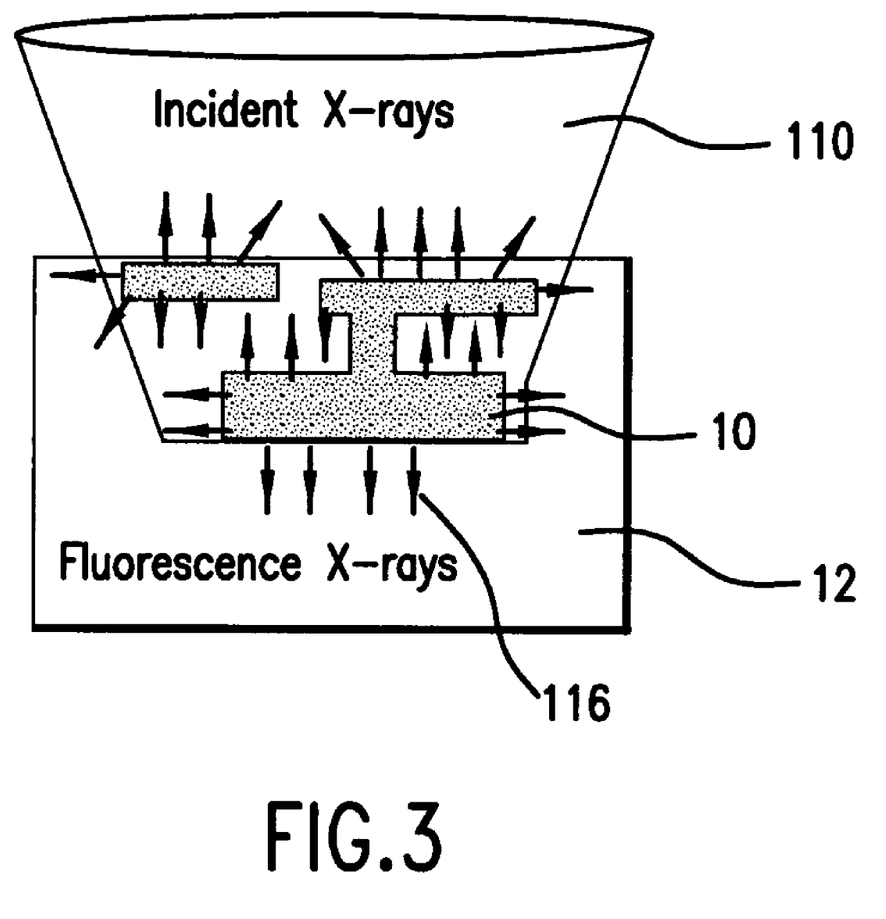
FIG. 3 schematically illustrates fluorescence imaging of structures containing a particular element in an integrated circuit using the x-ray fluorescence imaging mode.

As illustrated in FIG. 2, the primary radiation 110 causes an inner-shell electron (1) in the element of interest to be ejected (ionization). The vacancy (2) so created in the inner-shell is filled by an electron (3) in an outer electron shell (4). This transition generates either photons of a corresponding energy, or Auger electrons. The photons emitted constitute the secondary or fluorescence radiation 116 from the element of interest, such as the copper that forms the traces in an IC 10 of wafer 12, as illustrated in FIG. 3.

Returning to FIG. 1, other radiation may be coming from the test object 10, such as secondary radiation from other elements, reflected or scattered primary radiation, and the bremstrahlung radiation generated by photoelectrons that have been ejected by the primary radiation.

An imaging system 105 minimally includes a lens 118 and a detector system 122. The lens 118 is used to create a focused beam 120 of the secondary radiation 116 from the element of interest onto the detector system 122.

In one implementation, the detector system 122 is a two dimensional array of elements, such as a charge coupled device (CCD) detector array. Depending on the energies involved, a scintillator may also be required to convert X-rays into light, which is then imaged by a suitable detector array with appropriate imaging optics. In another implementation, the detector system 122 is a detector with no spatial resolution, such as a single element solid state detector. In some implementations, the detector system further has energy resolution.

According to the present embodiment of the invention, the lens 118 is selected to preferentially image the secondary X-ray radiation 116 from only (typically) the element of interest onto the detector system 122. Specifically, the lens 118 is a chromatic lens that effectively focuses only a narrow band of energies, i.e., the energies around the fluorescence line of the element of interest, onto the detector system 122. This is achieved by using a lens in which the focal length depends on energy and by suitably arranging the distances between the object 10 and the lens 118 (distance L1), and the lens 118 and the detector system 122 (distance L2) so that the normal imaging condition is only satisfied for that narrow band of energies.

In the present implementation, the lens 118 is a zone plate lens. Generally, the focal length of a zone plate lens is linearly dependent on energy. The energy bandwidth ($\Delta E/E$) is approximately given by the equation $\Delta E/E = 2V/D$, where D is the zone plate lens diameter, and V the effective field of view of the X-ray fluorescence microscope.

The effective field of view can be designed to a desired value by controlling the size of the primary ionizing radiation or using a pupil aperture in the optical train, e.g., the aperture 126 in FIG. 1. The zone plate diameter is preferably designed to achieve a required energy resolution for a given field of view. Radiation with energies outside the energy bandwidth will be out of focus at the detector plane.

The pupil aperture 126 is typically located between the lens 118 and the detector, and preferably in near proximity to the detector. However, in other applications, the pupil aperture is located between the lens 118 and the object of interest 10.

The energy bandwidth ΔE/E can be improved by using a zone plate that has a diffraction efficiency that peaks in a narrow energy band at the x-ray fluorescence energy.

In the present implementation, the lens 118 is preferably a zone plate lens that includes the element of interest. Preferably, the zone plate lens 118 is made of a compound, e.g., alloy, consisting substantially of the element of interest. In other cases, the zone plate lens is made solely of the element of interest. In still other cases, the zone plate lens 118 is made from a compound comprising the element of interest.

For example, if the element of interest is copper, i.e., the operator is seeking to image the copper structures of an IC such as in FIG. 3, for example, a copper or copper-containing zone plate lens 118 is used. Generally, the absorption of its own fluorescence X-rays by an element is near a local minimum over a finite energy range near the fluorescence X-ray energy, and this property can generally be used to construct a zone plate lens using a compound including the element of interest to obtain a high diffraction (focusing) efficiency.

For a large number of elements, such as the elements with atomic numbers between 4–30, the diffraction (focusing) efficiency of a zone plate lens can be made to peak at the fluorescence X-ray energy of the element of which the zone plate is made. This is achieved for fluorescence X-ray energies less than about 1 keV in the present implementation by making use of the change in the real part of the atomic scattering factor of an element, which decreases from a positive value to a negative value near the fluorescence X-ray energy. This is typically several electron-Volts less than that of an absorption edge of the element.

Figure 4:
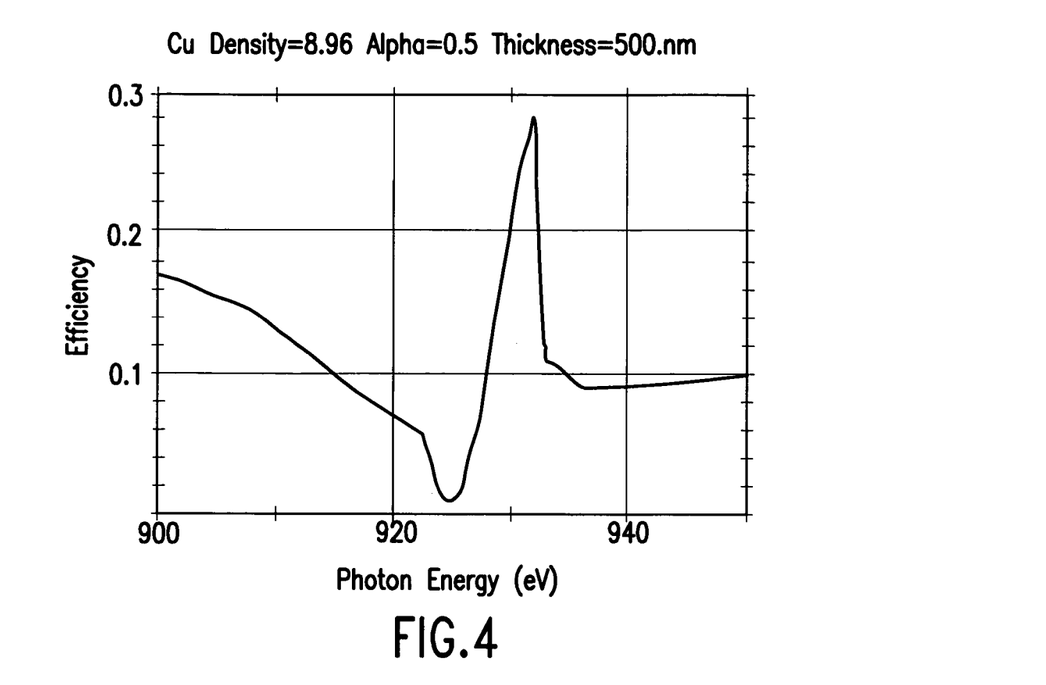
FIG. 4 is a plot of the efficiency of a 500 nanometer copper zone plate as a function of photon energy in electron-Volts (eV), illustrating that a peak diffraction efficiency is obtained near Cu Lα radiation energy at ~930 eV.
Figure 6:
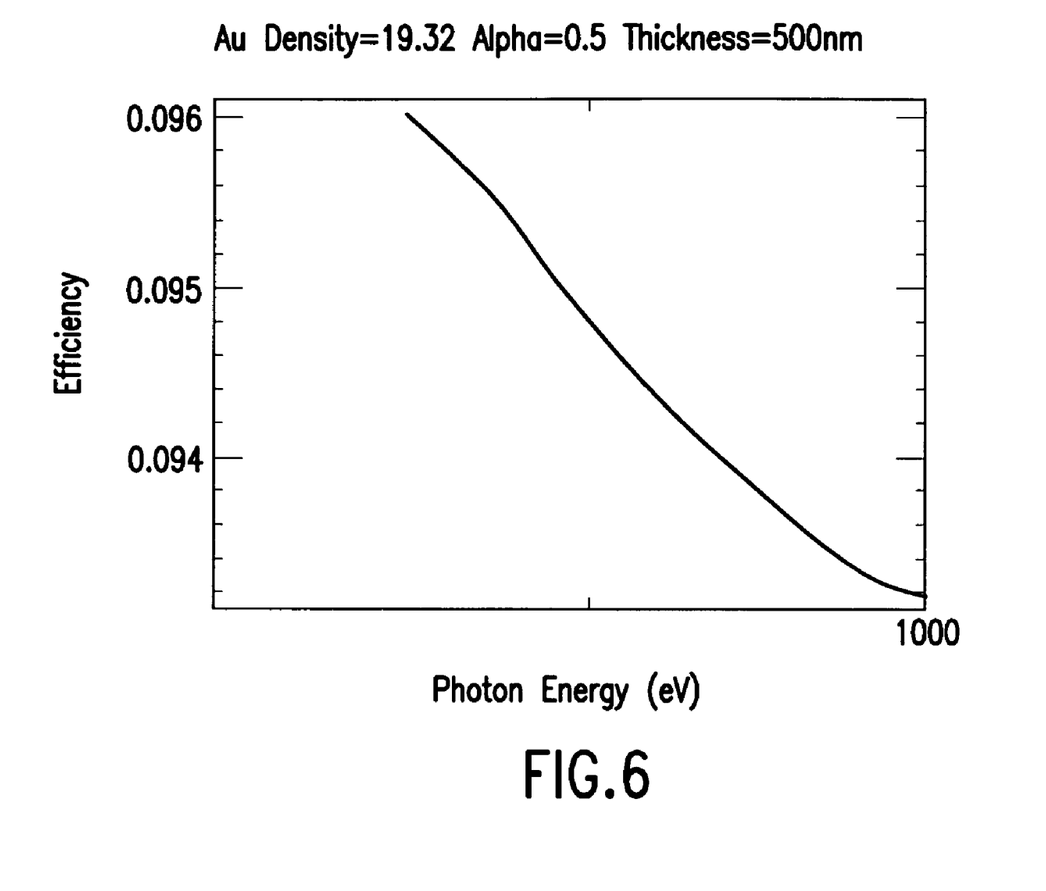
FIG. 6 is a plot of the efficiency of a 500 nanometer gold zone plate as a function of photon energy in electron-Volts, illustrating slow variation of diffraction efficiency over 800–1000 eV energy range.

FIG. 4 shows an example implementation where a Cu zone plate is designed to have its diffraction efficiency to peak at 932 eV, which is approximately the energy of a Cu Lα fluorescence line. In comparison, a gold zone plate would have an efficiency at the copper fluorescence line (930 eV) of about 10%, and would vary very little from this value from 850 to 1000 eV (see FIG. 6).

With reference to FIGS. 4 and 1, the preferential imaging is enhanced when the zone plate is produced using a compound comprising, and preferably comprising substantially, the same element, because of the combined effect of the loss of diffraction efficiency and out of focusing for x-ray energies away from the x-ray fluorescence line of interest.

Consider a 500-nm thick copper zone plate designed for the 930 eV copper fluorescence line with a focal length of 1 centimeter and an outermost zone width of 50 nm. The wavelength is about 1.3 nm. At 905 eV, the copper zone plate lens will have a focal length of 9.73 millimeters. The depth of focus is a few micrometers, so the image plane for fluorescence occurring at 905 eV is substantially out of focus and well away from the image at 932 eV. The focusing efficiency of the zone plate at 905 eV is about half of that for 930 eV, further reducing its contribution to the background intensity on the image formed by the 930 Cu Lα fluorescence x-rays.

Generally, the spatial resolution of a zone plate-based X-ray fluorescence imaging microscope is $k1 \lambda/(NA)$; depth of focus=$k2 \lambda/(NA)^2$; $k1=k2=\frac{1}{2}$, corresponding to the usual definition of diffraction-limited imaging.

To further cut-off higher energy radiation from the test object, a plate 124 containing suitable elemental composition, such as the element of interest for an x-ray energy less than 2 keV, is added in series with the zone plate lens 118 in some embodiments. Fluorescing materials are relatively transparent for their own fluorescence energies, but absorption is quite high above the absorption edge (see FIG. 5), resulting in a low-pass transmission characteristic, which reduces the amount of X-rays with energies higher than the X-ray fluorescence energy that are transmitted to the detector 122. Of course, the zone plate lens 118 itself becomes absorbing above the absorption edge, but the zones cover only about 50% of its area.

Zone plate lenses comprising other constituent elements for imaging of these elements are possible. The following sets forth the parameters for zone plates with 1 cm focal length, 50 nm finest zone:

| Element | energy (eV) | wavelength (nanometers) | diameter (millimeters) | number of zones |
|---------|-------------|-------------------------|------------------------|-----------------|
| B  | 183    | 6.78  | 1.36  | 6820 |
| Cu | 930    | 1.33  | 0.266 | 1330 |
| As | 1282 (1317) | 0.967 | 0.193 | 967  |
| Al | 1486   | 0.833 | 0.166 | 833  |
| Ta | 1710   | 0.724 | 0.145 | 724  |
| Si | 1740   | 0.712 | 0.143 | 712  |
| P  | 2013   | 0.615 | 0.123 | 615  |
| Cu | 8048   | 0.154 | 0.031 | 156  |

It is recognized that it is important to use low attenuation materials for the membrane, on which the zone plate is fabricated, especially for low energy fluorescence imaging applications, such as boron. A large diameter is needed to compensate for a low fluorescence rate. The zone plate substrate should, therefore, not be silicon nitride, since for such a large window it would have to be thick, which would render it highly absorbing. An appropriate substrate would be boron nitride, which is a material that provides substantially more attenuation than B, i.e., greater than 90%, but is more radiation sensitive than silicon nitride.

Also, there is a concern about choosing the energy of the exciting radiation to be too close to the fluorescence energy, for example As with W L beta for Cu K. In this case, it is more difficult to discriminate against scattering and Compton radiation, than if the excitation were at higher energy. Of course, the absorber helps, but it can also be a secondary source of fluorescence.

Finally, it should be noted that there is a need for a central stop to block zeroth order radiation.

Figure 7:
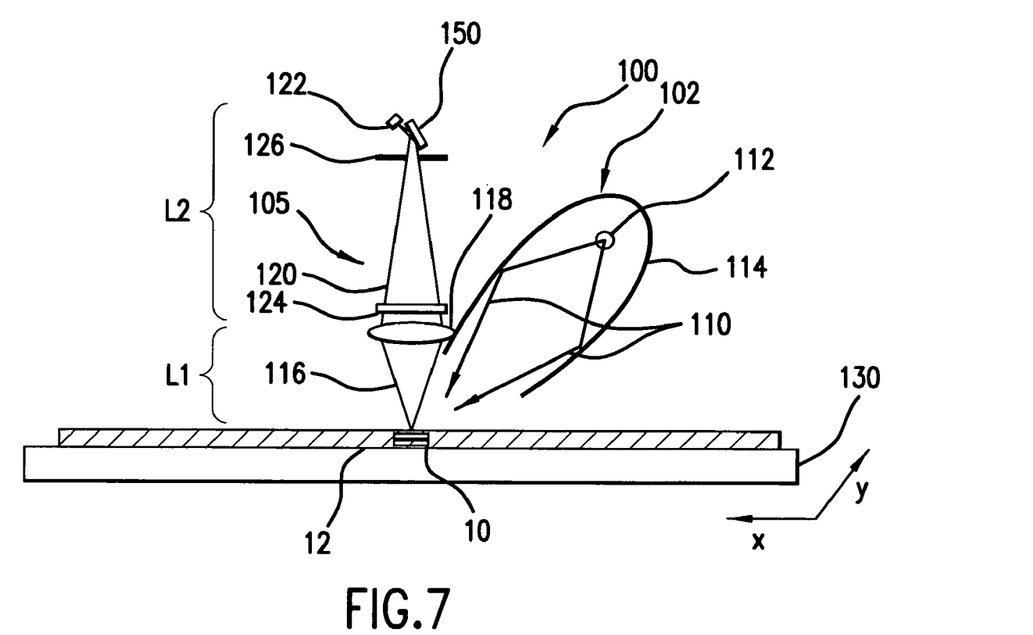
FIG. 7 is schematic diagram of an X-ray fluorescence microscope according to another embodiment in which a wavelength dispersive optic is used with a chromatic or achromatic lens to achieve element-specific imaging.

FIG. 7 shows another embodiment of an X-ray fluorescence microscope 100 according to the present invention. Here, the preferential imaging is achieved by inserting a suitable spectral filter 150 in the imaging system 105. The filter is selected to pass, i.e., reflect, a narrow spectral band centered on the fluorescence line of the element of interest. In one implementation, the spectral filter 150 is a multilayer optic or a crystal.

In this embodiment, the imaging optic 118 is either a chromatic lens, such as a zone plate, or an achromatic optic, such as a Wolter optic. The spectral filter 150 is configured so that the imaging condition between the object 10, and the lens 118, and the detector 122 is maintained.

Generally, the combination of a chromatic lens 118 and the spectral filter 150 leads to better performance as to the preferential imaging property of the x-ray fluorescence microscope.

Figure 8:
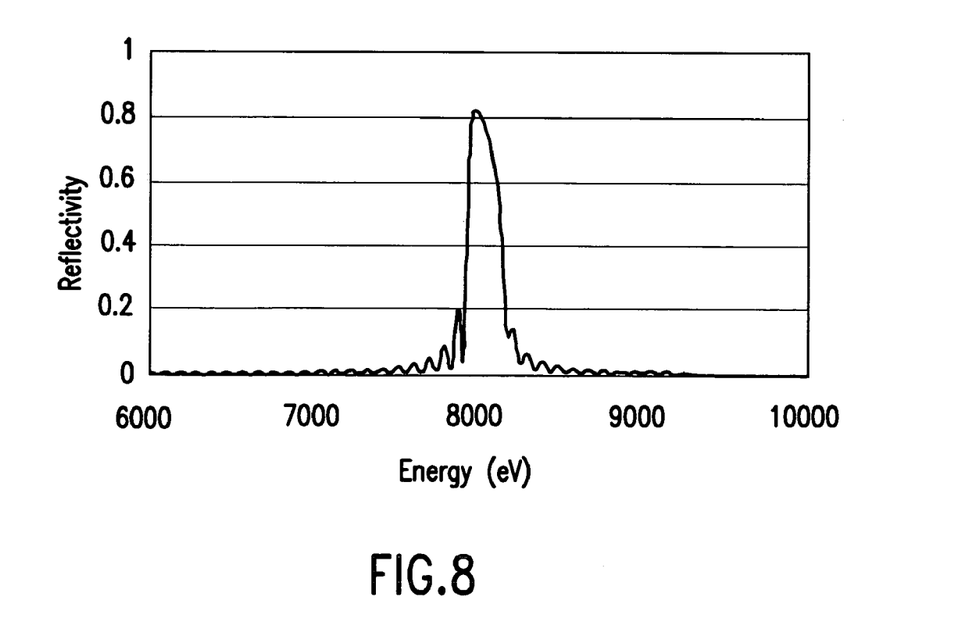
FIG. 8 is a plot of x-ray reflectivity of a multilayer optic including an 80 layer pairs of tungsten and carbon deposited on a flat substrate, assuming a grazing incidence angle of 1.81 degree and multilayer period of 2.5 nm.

FIG. 8 shows the x-ray reflectivity of an exemplary multilayer filter or optic 150 that is designed and arranged to reflect efficiently a narrow energy band of x-rays near the Cu Kα (8046 eV) fluorescence x-rays. For a given multilayer or crystal, it reflects the fluorescence x-rays of interest efficiently only within a finite angle of incidence (angular acceptance). To avoid the reduction of throughput and maintain the resolution of the x-ray fluorescence microscope due to the finite angular acceptance, it is important to place the multilayer optic or crystal away from the lens 118 and close to the detector 122, because the angular divergence of the imaging forming fluorescence x-ray beam decreases as the distance from the lens 118 increases and thus reduces the required angular acceptance of the multilayer or crystal optic for high throughput.

The depth of the object to be explored depends on the energy of the primary and fluorescence radiation, and on the geometry. Generally, lower energy radiation is less penetrating, and leads to a shallower object volume. By adjusting the angle of incidence and the angle of collection of fluorescence relative to the surface normal, the depth probed is adjustable.

The type of the primary ionizing radiation 110 can be optimized based on specific applications. In general, X-rays offer a significantly higher ratio of fluorescence X-rays to background signal than electrons. X-rays also offer other advantages such as applicability to all materials, because there is no charging effect and they are usable in an ambient environment, i.e., no vacuum requirement.

Figure 9:
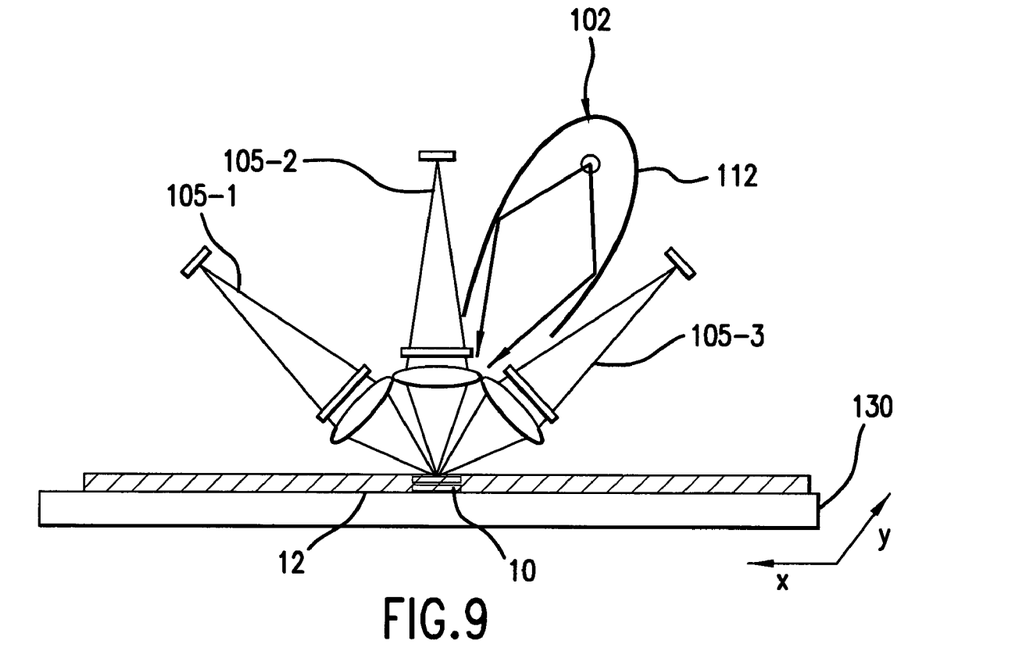
FIG. 9 is schematic diagram of an X-ray fluorescence microscope according another embodiment in which multiple imaging systems are used in parallel to increase throughput, or perform stereo and tomographic three-dimensional imaging, or simultaneously image multiple elements.

FIG. 9 shows another embodiment that is capable of imaging multiple elements of interest at the same time. Specifically, multiple imaging systems 105-1, 105-2, 105-3 are directed to image approximately the same or the same volume in the test object 10. Each imaging system 105-1, 105-2, 105-3 is configured to image fluorescence X-ray lines of different elements. Therefore, in one specific example, the zone plate lenses of each imaging system 105-1, 105-2, 105-3 comprise different constituent materials.

According to still another embodiment, the system of FIG. 9 is configured for increased throughput. Each imaging system 105-1, 105-2, 105-3 is configured to image the same fluorescence line and is aimed to image adjoining or adjacent volumes of the test object.

According to another embodiment, a set of element-specific two dimensional (2D) images is collected over a large range of angles and reconstructed using tomographic reconstruction. This yields an element-specific three-dimensional (3D) image. A simple implementation of this method collects two 2D stereo image pairs with an angular separation of about 10 degrees and the stereo information of the object can be viewed using stereo viewing technology. The collection of the 2D images can be obtained using several identical imaging systems 105, which image approximately the same volume in the test object.

EXAMPLES

The X-ray fluorescence from important materials of an IC are induced with radiation energy in the approximately 100 to 8000 eV range. The materials that produce the x-ray fluorescence are copper at 930 eV (La) and 8046 eV (Ka), silicon at 99 eV (La) and 1740 eV (Ka), germanium at 1186 eV (La), tantalum at 1710 eV (Ma), titanium at 452 eV (La) and 4510 eV (Ka), cobalt at 776 eV (La) and 6929 eV (Ka), phosphorus at 2013 eV (Ka), arsenic at 1282 eV (La), and aluminum at 1486 eV (Ka), for example. Boron at 183 eV (Ka) is another alterative.

Considering copper as an example, FIG. 4 shows the efficiency of a 500 nanometer (nm) copper zone plate in the 900 to 950 eV range, where copper has a fluorescence line. Note that the efficiency peaks to about 30% around 932 eV, which is close to the energy of a Cu La fluorescence line at 930 eV.

Figure 5:
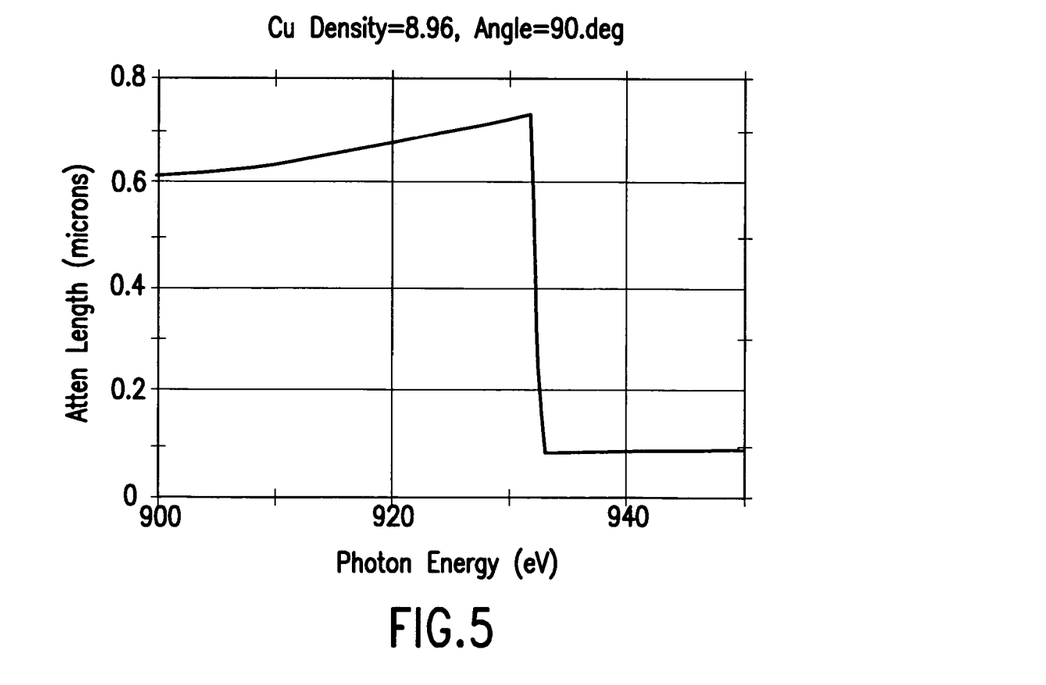
FIG. 5 is a plot of attenuation length in micrometers as a function of photon energy in electron-Volts for copper illustrating high transmission of Cu Lα fluorescence x-rays and abrupt increase in absorption for x-rays of energy greater than the Cu L absorption edge at ~933 eV.

FIG. 5 shows the transmission of copper over this 900 to 950 eV range. For example, 200 nm of copper has a transmission above 933 eV of only 8%, but a transmission of 75% where the grating efficiency is high. The abrupt change in transmission is due to the absorption edge of copper and fluorescence is emitted at an energy slightly below this edge, i.e, at about 930 eV.

As a result, a solid plate 124 of copper, which is 200 nanometer (nm) thick, combined with a 500 nm thick zone plate lens 118 will have a focusing efficiency of about 20% at 930 eV and less than 1% above about 933 eV. Below 930 eV, the efficiency falls to less than 1% at 925 eV. It remains below 10% until the energy has fallen to about 905 eV.

While the diffraction efficiency recovers at lower energies, the focal length of the zone plate is now significantly changed from that at the fluorescing energy—any radiation such as fluorescence radiation at this energy (from other materials) is not imaged on the detector array 122. It should be noted that the number of elements used in IC fabrication is typically limited and thus the characteristic fluorescence lines are widely spaced, so the element specific character of the zone plate lens made of the fluorescing material will not be compromised in most situations.

An example application is to image Cu structures in an IC, such as interconnects, and vias, and defects associated with them. It is beneficial to use the Cu La X-ray fluorescence line for this application. The primary ionizing radiation is either an electron beam of energy greater than 1000 eV or an X-ray beam generated for example by electron bombardment of a solid target producing x-rays of energy greater than 940 eV. Specific applications include failure analysis of IC components, IC metrology and inspection in a production line.

In a different example, copper K alpha fluorescence at 8046 eV is used to image copper interconnect lines in IC packaging. The primary radiation is provided by electron bombardment of a solid anode capable of producing the required primary radiation, such as tungsten and gold anodes. The tungsten L beta lines around 9670 eV are efficient in inducing fluorescence in copper. This higher energy radiation can be used to explore packages up to several hundred micrometers thick. Zone plates fabricated using lithographic techniques may be limited in throughput for higher resolution applications because of limited solid angle acceptance.

The low solid angle acceptance can be addressed, however, by the following design. The focusing lens is made up of two linear zone plates oriented at right angles to each other. These linear zone plates are fabricated by sputtering alternating layers of appropriate materials (such as W and C) on a substrate, and slicing this multilayer structure to the thickness that gives maximum efficiency. This way, finest zones as small as 3 nanometers can be fabricated, and the resulting solid angle acceptance improved by a factor of 278 compared to zone plates with 50 nm finest zones. These optical elements are not likely to obtain 3 nanometer resolution, but they offer significantly larger solid angles of acceptance for high throughput at resolutions substantially larger than 3 nm. For example, a zone plate with a 3 nm finest zone width has a solid angle acceptance 100 times larger than a zone plate with a 30 nm finest zone width, and increases throughput by approximately 100 times for 30 nm resolution x-ray fluorescence imaging. Yet another example would involve the study of buried structures such as steel and other structural materials underneath coatings (applied by thermal spraying or otherwise). In this application a copper or tungsten anode is to be used to generate the primary radiation to excite fluorescence in iron, nickel, chromium, or cobalt. Again, the crossed linear zone plates would be preferred as the lens to study microcracking and corrosion, for example.

Yet another application is the imaging of biological specimens, such as bones and single biological cells. Spatial distribution of elements, such calcium and phosphorus in a bone or a cell, can be imaged in 2D or 3D using present invention. It is recognized that such imaging may be performed without significantly affecting the livelihood of the biological specimen under investigation and thus time lapse imaging may be taken to study development.

X-ray Fluorescence Backlighting Imaging Mode

Figure 10:
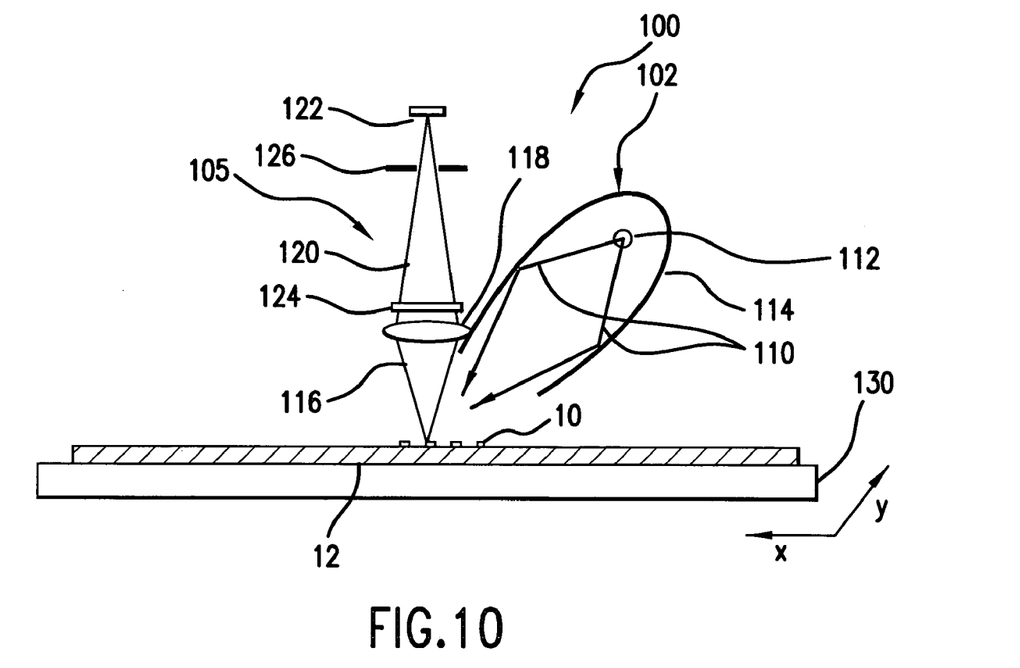
FIG. 10 is schematic diagram of an X-ray fluorescence microscope according another embodiment that operates in a backlighting mode.

FIG. 10 shows an X-ray fluorescence microscope 100 that is configured in an X-ray fluorescence backlighting imaging mode, according to the present invention. Specifically, the fluorescence that is imaged originates from the known structure 12 (such as the substrate, rather than from the object of interest 10. The object of interest 10 is positioned between the known structure 12 and the lens 118. The object of interest absorbs or scatters part of the characteristic X-ray radiation, and thus casts a shadow at the image plane.

In this mode of operation the elements present in the object are not directly identified, but if their composition is known, then the geometry of the object, such as the thickness and shape, can be determined from the image that contains the attenuation information of the backlighting. Other image contrast enhancement methods, such as the Schilieren method, can be employed to increase image contrast of materials of low absorption contrast.

For example, silicon L alpha or K alpha fluorescence x-rays are used in one application as backlighting to image IC structures above a silicon substrate, such as Cu interconnect lines and vias, Ta-containing diffusion barriers, interlayer dielectrics, and polysilicon gate contacts. It is recognized that silicon is a preferred material for making zone plates of high focusing efficiency. Other preferred materials include molybdenum and rhodium for Si L alpha line and Au, W, and Ta for Si K alpha line.

For yet another example, the profile of etched structures produced in an IC production process can be studied using the x-ray fluorescence backlighting imaging mode. Backlighting by the x-ray fluorescence produced in the wafer 12 arrives at the lens 118 after being absorbed or scattered by the test object 10, which includes etched structures. The geometry of the etched structure 10, including its profile, together with the material composition of the etched structure, determines the effect on the backlighting fluorescence x-rays, and leads to measurable effects in the x-ray fluorescence image. It is recognized that for etched structures of a linear dimension not significantly larger than approximately 30 times of the wavelength of the fluorescence x-rays, and of an aspect ratio greater than approximately 3, the profile of the etched structure produces a significant effect on the angular distribution of the backlighting fluorescence x-rays due to the scattering effect. This effect increases with decreases in linear dimensions of the etched structure and increases in the aspect ratio. It is further recognized that the effect of the profile of the etched structure can be enhanced when the etched structure is suitably arranged, such as a periodic structure. It is beneficial in some implementations to use x-ray fluorescence line(s) of longer wavelength(s) and from element(s) contained in major IC fabrication materials, such as silicon, copper, oxygen, tantalum, and carbon.

For yet another example, Cu L alpha fluorescence line from Cu interconnect lines or vias is used to detect and image residuals and particles on top of them in an IC production process. In a preferred implementation, the zone plate is constructed using Cu.

For example, defects, such as contamination by resist residues or other contamination, on a mask used in IC fabrication can be seen by imaging the silicon fluorescence from the substrate 12, which may be silicon wafer material or a silicon compound, such as glass, quartz, or silicon nitride. The defect will show up as a deviation from the desired image of the clean and intact mask. In this imaging mode, the mask may be designed to be used either in transmission or in reflection.

Using a zone plate with 1 cm focal length, an area 0.1 mm on the side could be imaged in one exposure with 50 nm resolution onto a CCD detector. A full wafer would be explored in a step-and-repeat operation. Defect identification would be performed automatically by comparing the digital images with the standard stored in the control computer.

Another application is the inspection of coatings, such as thermal coating for improving surface operating temperature, hardness coating for improving surface hardness, and painting for improving surface chemistry resistance to erosion. Using fluorescence radiation from the bulk material underneath the coating, the image will clearly show non-uniformities, pinholes, cracks and other defects.

Fluorescence Spectrometer Mode

With reference to FIG. 1, in the fluorescence spectrometer mode, the object-to-lens distance L1 and the lens-to-detector distance L2 are adjusted so that all the characteristic fluorescence of a given element falls upon a single-element detector or is integrated over all the pixels in a two-dimension imaging detector 122. X-ray spectrum can be measured by scanning the chromatic lens such as zone plate along the axis connecting the center of the object 10 and the center of the detector 122 or the pupil aperture 126. Several of these spectrometers can be configured so as to monitor multiple elements simultaneously as described in connection with FIG. 9.

Because the numerical aperture of the lens used is inversely proportional to the energy, both the solid angle acceptance and the energy resolution of the instrument improve for lower energies. This is an important advantage over both energy dispersive and wavelength dispersive spectrometers, since the fluorescence yield drops with energy and the energy resolution of typical solid state energy dispersive detectors are often too limited for low energy x-ray analysis applications.

This arrangement is applicable to the monitoring of the dose of the shallow doping of semiconductor material with boron, phosphorus, and/or arsenic. High spatial resolution is generally not desired in this case, so the zone plate is used in a geometry yielding a convenient working distance and throughput. The area to be investigated can be defined using an aperture in front of the single-element detector. The observed count-rate, after matrix and element dependent calibration factors and correction for background will be directly proportional to the amount of the dopant within the probed volume.

Another example that takes advantage of the imaging property of the lens for film thickness measurement is based on the recognition that the imaging property allows both the probed area and the solid angle of fluorescence collection to be well defined, thus permitting accurate determination of the number of fluorescing atoms in the probed volume. If the probed volume is a known, uniform thickness (film), then its film thickness can be determined. Example applications include measuring the film thickness of various materials in an IC production line, such as Cu, diffusion barrier, and interlayer dielectric layers.

While this invention has been particularly shown and described with references to preferred embodiments thereof, it will be understood by those skilled in the art that various changes in form and details may be made therein without departing from the scope of the invention encompassed by the appended claims. For example, typical scanning electron microscopes (SEM) have X-ray detectors (EDAX), which are used to identify materials being imaged. In the fluorescence spectrometer mode, the present invention is used as an element specific imaging attachment to a SEM.

What is claimed is:

1. A microscope system comprising:
   a scanning electron microscope for generating an electron beam operating with electron energy greater than an absorption-edge energy of an element of interest and irradiating a test object to induce secondary fluorescence X-ray radiation from the element of interest;
   an image detector comprising a detector array with a two dimensional array of elements; and
   a zone plate lens for selectively imaging the secondary fluorescence X-ray radiation, generated by the electron beam of the scanning electron microscope, from the element of interest onto the image detector.

2. A microscope system as claimed in claim 1, wherein the lens is a chromatic lens.

3. A microscope system as claimed in claim 1, further comprising a spectral filter.

4. A microscope system as claimed in claim 3, wherein the spectral filter is a multilayer optic.

5. A microscope system as claimed in claim 3, wherein the spectral filter is a crystal.

6. A microscope system as claimed in claim 1, further comprising a pupil aperture for improving preferential imaging of the secondary radiation.

7. A microscope system as claimed in claim 1, wherein the zone plate lens has a high diffraction efficiency for an energy of a fluorescence line of the element of interest.

8. A microscope system as claimed in claim 1, wherein the lens is made of a compound including the element of interest.

9. A microscope system as claimed in claim 1, wherein the element of interest is aluminum and the lens comprises aluminum.

10. A microscope system as claimed in claim 1, wherein the element of interest is copper and the lens comprises copper.

11. A microscope system as claimed in claim 1, wherein the element of interest is tantalum and the lens comprises tantalum.

12. A microscope system as claimed in claim 1, wherein the element of interest is phosphorus and the lens comprises a phosphorus compound.

13. A microscope system as claimed in claim 1, wherein the element of interest is boron and the lens comprises a boron compound.

14. A microscopic imaging method, comprising:
    irradiating a test object with an electron beam of a scanning electron microscope;
    selectively imaging induced secondary fluorescence X-ray radiation from the test object, being generated by the electron beam of the scanning electron microscope, with a chromatic lens; and
    detecting the secondary fluorescence X-ray radiation imaged by the chromatic lens using an image detector with a two dimensional array of elements.

15. A method as claimed in claim 14, further comprising aperturing the secondary fluorescence X-ray radiation prior to detecting the secondary fluorescence X-ray radiation to improve preferential imaging of the secondary radiation.

16. A method as claimed in claim 14, wherein the chromatic lens is a zone plate lens.

17. A method as claimed in claim 16, wherein the zone plate lens has a high diffraction efficiency for an energy of a fluorescence line of an element of interest.

* * * * *